(12) United States Patent
Carlon et al.

(10) Patent No.: US 6,501,980 B1
(45) Date of Patent: Dec. 31, 2002

(54) EASILY DECONTAMINATED MRI ENDOCAVITY COILS

(75) Inventors: John T. Carlon, Madison; Benjamin R. Stern, Willoughby Hills, both of OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/710,373

(22) Filed: Nov. 9, 2000

(51) Int. Cl.⁷ ................................................. A61B 5/05
(52) U.S. Cl. ....................................... 600/423; 324/318
(58) Field of Search ................................ 600/410, 423; 324/307, 309, 318, 322; 128/898

(56) References Cited

U.S. PATENT DOCUMENTS

| | | | |
|---|---|---|---|
| 3,462,335 A | 8/1969 | Hansen et al. ............... | 156/272 |
| 5,050,607 A | 9/1991 | Bradley et al. ......... | 128/653 A |
| 5,281,214 A * | 1/1994 | Wilkins et al. ............... | 606/13 |
| 5,348,010 A | 9/1994 | Schnall et al. ............ | 128/653.2 |
| 5,355,087 A | 10/1994 | Claiborne et al. .......... | 324/322 |
| 5,370,614 A * | 12/1994 | Amundson et al. .... | 604/103.02 |
| 5,451,232 A | 9/1995 | Rhinehart et al. .......... | 606/192 |
| 5,465,709 A * | 11/1995 | Dickie et al. ............... | 600/223 |
| 5,476,095 A | 12/1995 | Schball et al. ............ | 128/653.2 |
| 5,569,163 A * | 10/1996 | Francis et al. ............... | 359/510 |
| 5,676,255 A * | 10/1997 | Flowers ........................... | 209/2 |
| 5,738,677 A * | 4/1998 | Colvard et al. ............. | 128/898 |
| 5,860,425 A * | 1/1999 | Benderev et al. ........... | 128/898 |
| 5,902,251 A * | 5/1999 | vanHooydonk ............. | 600/549 |
| 6,051,974 A | 4/2000 | Reisker et al. .............. | 324/318 |
| 6,096,022 A * | 8/2000 | Laymond et al. ........... | 604/523 |
| 6,231,564 B1 * | 5/2001 | Gambale .................... | 600/585 |

FOREIGN PATENT DOCUMENTS

EP    0919824 A2    6/1999
JP    09103415    4/1997

OTHER PUBLICATIONS

N.M. deSouza, et al. "Magnetic Resonance Imaging of the Anal Sphincter Using an Internal Coil" *Magnetic Resonance Quarterly* vol. 11, No. 1, pp 45–56, 1995.

Safety and Patient handling Chap., Operator's manual of the Phillips MR GYROSCAN system Jul. 1992.

Operating instructions for the MRInnervu Mar. 1990.

(List continued on next page.)

*Primary Examiner*—Marvin M. Lateef
*Assistant Examiner*—Eleni Mantis Mercader
(74) *Attorney, Agent, or Firm*—Fay, Sharpe, Fagan, Minnich & McKee, LLP (57) ABSTRACT

An endocavity RF coil assembly for an MRI apparatus includes a reusable probe (30). The reusable probe has a sealed hollow outer housing or cover having a closed distal end and an open proximate end (83). The distal end is formed to fit into a cavity of a subject being examined. An active RF coil element (62) is connected with a circuit board located within the outer housing. The housing includes a plurality of ABS plastic pieces (64, 66, 74; 100, 102, 108) that have mating surfaces that are surface treated to break polymer chains at the surface. An epoxy (132) bonds to the polymer chain ends to connect the pieces. An over-molded form (82) is connected to the proximate end (83) of the outer cover or housing. The over-molded form (82) is arranged such that it seals the proximate end (83) of the outer cover (100) closed. In order to make the coil assembly more assuredly sterilizable, the epoxy completely fills the seams and optionally forms a projection bead (134) in order to smooth over and assure crevice free junctions. Crevices can shelter microbes from liquid and gaseous sterilants jeopardizing assurance that the sterilization process killed all the microbes.

12 Claims, 6 Drawing Sheets

OTHER PUBLICATIONS

Boeda, et al. "Application des plasmas froids au traitement de surface des polymères", Revue Générale de l'Electricite (RGE) Paris, FR, No. 5 May 1, 1987 pp. 15–21 XP000006613.

Sun, et al. "Corona Treatment of Polyolefin Films—A Review", Advances in Polymer Technology, John Wiley & Sons, Chichester, GB, vol. 18, No. 2, Jul. 21, 1999 pp. 171–180 XP000849023.

* cited by examiner

EASILY DECONTAMINATED MRI ENDOCAVITY COILS

BACKGROUND OF THE INVENTION

The present invention relates to the magnetic resonance imaging arts. It finds particular application in conjunction with medical magnetic resonance imaging systems and will be described with particular reference thereto. It is to be appreciated, however, that the present invention may also find application in conjunction with other types of magnetic resonance imaging systems, magnetic resonance spectroscopy systems, and the like.

In magnetic resonance imaging, a substantially uniform main magnetic field is generated within an examination region. The main magnetic field polarizes the nuclear spin system of a subject being imaged within the examination region. Magnetic resonance is excited in dipoles which align with the main magnetic field by transmitting radio frequency excitation signals into the examination region. Specifically, radio frequency pulses transmitted via a radio frequency coil assembly tip the dipoles out of alignment with the main magnetic field and cause a macroscopic magnetic moment vector to precess around an axis parallel to the main magnetic field. The precessing magnetic moment, in turn, generates a corresponding radio frequency magnetic signal as it relaxes and returns to its former state of alignment with the main magnetic field. The radio frequency magnetic resonance signal is received by the radio frequency coil assembly, and from the received signals, an image representation is reconstructed for display on a human viewable display.

In certain medical MRI applications, it is advantageous to perform imaging scans over a limited field of view and depth of penetration of specific regions of the patient being examined. Such regions may include the anus, the prostate, the cervix, and other regions associated with internal cavities of a patient. RF receive coils of the intracavitary or endocavitary type are generally used to image these regions as the proximity of the coils in such applications provides improved signal-to-noise ratio over a limited field of view and depth of penetration.

Previously, intracavitary or endocavitary RF receive coils made use of an active RF coil element contained within an inflatable non-permeable balloon. An electrical cable interfaced the active RF coil to external electrical circuitry that was used to interface the coil with the magnetic resonance imaging system. The device would be inserted into a cavity associated with the region of interest, for example a patients rectum, and the balloon would then be inflated. Finally, the external electrical interface would be used to tune and match the coil to the MRI system. Typically, such endocavitary coils were disposable and would not be reused for multiple scans. Additionally, the active RF coil element was not rigidly formed, and as such, each individual probe had to be tuned and matched.

Another previous form of an endocavitary probe was reusable for a limited number of times before disposal. This form employed a loose latex sheathing or over cover which was disposed after each patient. However, the device was reused for only a limited number of times.

Other types of reusable coils are constructed of medical grade plastic. Such coils are subject to surface disinfection after each use. Coils which are encased in the plastic are typically immersed in a liquid disinfectant or sterilant, such as alcohol, hydrogen peroxide, or the like after each use.

Because these coils come in contact with mucus membranes and blood barriers, high level disinfection or sterilization are desirable. Heat sterilization tends to degrade plastic parts and may harm on board electronics. Balloons are particularly sensitive to heat degradation. The coils are often constructed of multiple pieces of plastic, and thus has seams where the pieces meet. Microscopic organisms can become lodged in these crevices where liquid sterilants cannot assuredly eliminate them.

The present invention contemplates a new and improved endocavity RF coil assembly for an MRI apparatus which overcomes the above referenced disadvantages and others.

SUMMARY OF THE INVENTION

In accordance with one aspect of the present invention, an endocavity RF coil assembly for an MRI apparatus is provided. The endocavity RF coil assembly includes a reusable probe. The reusable probe includes a hollow outer housing having a closed distal end and an open proximate end. The distal end is formed to fit into a cavity of a subject being examined. An active RF coil element is rigidly formed about an internal sleeve which is located within the distal end of the outer cover. A tuning and matching circuit disposed within the outer cover on the proximate end side of the active RF coil element is arranged on a printed circuit board and attached to the active RF coil element. An over-molded form is connected to the proximate end of the outer cover. The over-molded form is arranged such that it seals the proximate end of the outer cover closed. The probe includes an epoxy coating.

In accordance with a more limited aspect of the present invention, the endocavity RF coil assembly includes a non-magnetic magnetic RF cable connected to the tuning and matching circuit. The non-magnetic RF cable extends out of the open proximate end of the outer cover through the over-molded form to a preamplifier of the MRI apparatus. The RF cable has an outer cable insulation and a an MR compatible and biocompatible outer jacket extruded over the outer cable insulation.

In accordance with a more limited aspect of the present invention, the over-molded form and the outer jacket of the RF cable are both made out of a PVC plastic which forms a seal therebetween.

In accordance with a more limited aspect of the present invention, the internal sleeve and the outer housing are made form a medical grade ABS plastic.

In accordance with a more limited aspect of the present invention, the endocavity RF coil assembly includes a plurality of grooves cut into the outer surface of the outer housing at a proximate end. The grooves are arranged to completely encircle the outer cover such that a portion of the over-molded form is embedded therein sealing the connection between the over-molded form and the outer housing.

In accordance with a more limited aspect of the present invention, some of the plurality of grooves are arranged with flat surfaces such that the over-molded form embedded therein prevents the over-molded form from rotating with respect to the outer housing.

In accordance with a more limited aspect of the present invention, the over-molded form is a polyhedron having a plurality of sides. The plurality of sides are each indexed with a representative indicia that indicates the orientation of the active RF element within the subject being examined.

In accordance with a more limited aspect of the present invention, the over-molded form is in the shape of a sphere.

In accordance with a more limited aspect of the present invention, the probe includes material which emits a limited magnetic resonance signal which is used to track the position of the probe relative to the subject being examined.

In accordance with a more limited aspect of the present invention, the printed circuit board is positioned and electronic components are located thereon such that image anomalies caused thereby are eliminated.

One advantage of the present invention is that the probe is reusable.

Another advantage of the present invention is that it can be manufactured to meet the electrical and mechanical required compliance standards such as UL 544 and IEC 601.

Another advantage of the present invention is that external circuitry for performing tuning and matching adjustments on a per-patient basis is eliminated.

Another advantage of the present invention is the prevention of the ingress of fluids into the interior of the reusable probe.

Another advantage of the present invention is the protection of subjects from RF burn.

Yet another advantage resides in the ease of sterilization.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts. The drawings are only for purposes of illustrating a preferred embodiment and are not to be construed as limiting the invention.

DETAILED DESCRIPTION OF THE PREFERRED EMBODIMENTS

Figure 1:
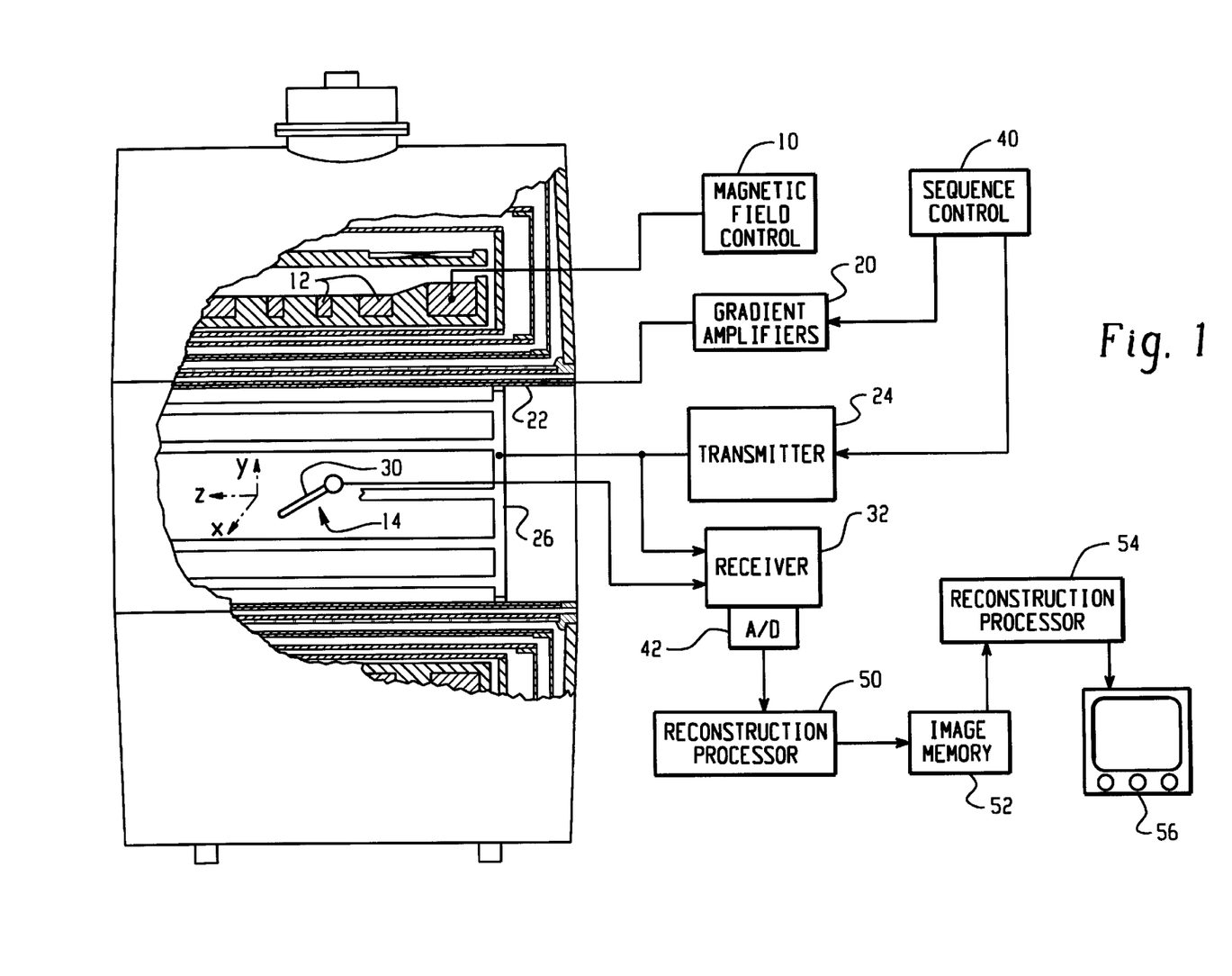
FIG. 1 is a diagrammatic illustration of a MRI apparatus in accordance with the present invention.

With reference to FIG. 1, a main magnetic field control 10 controls superconducting or resistive magnets 12 such that a substantially uniform, temporally constant main magnetic field is created along a z axis through an examination region 14. A magnetic resonance generation and manipulation system applies a series of radio frequency (RF) and magnetic field gradient pulses to invert or excite magnetic spins, induce magnetic resonance, refocus magnetic resonance, manipulate magnetic resonance, spatially and otherwise encode the magnetic resonance, to saturate spin, and the like to generate magnetic resonance imaging and spectroscopy sequences. More specifically, gradient pulse amplifiers 20 apply current pulses to selected ones or pairs of whole-body gradient coils 22 to create magnetic field gradients along x, y and z-axes of the examination region 14. A digital radio frequency transmitter 24 transmits radio frequency pulses or pulse packets to a whole-body RF coil 26 to transmit RF pulses into the examination region. A typical radio frequency pulse is composed of a packet of immediately contiguous pulse segments of short duration which taken together with each other and any applied gradients achieve a selected magnetic resonance manipulation. The RF pulses are used to saturate, excite resonance, invert magnetization, refocus resonance, or manipulate resonance in selected portions of the examination region. For whole-body applications, the resonance signals are commonly picked up by the whole-body RF coil 26.

For generating images of limited regions of the subject, local coils are commonly placed contiguous to the selected region. For example, a receive-only local radio frequency coil can be used to receive resonance signals introduced by body-coil RF transmissions, such as an endocavitary RF coil assembly probe 30. The resultant radio frequency signals are picked up by the whole-body RF coil 26 or other specialized RF coils and demodulated by a receiver 32 preferably including a preamplifier (not illustrated).

A sequence control circuit 40 controls the gradient pulse amplifiers 20 and the transmitter 24 to generate any of a plurality of multiple echo sequences such as echo planar imaging, echo volume imaging, gradient and spin echo imaging, fast spin echo imaging, and the like. For the selected sequence, the receiver 32 receives a plurality of data lines in rapid succession following each RF excitation pulse. An analog-to-digital converter 42 converts each data line to a digital format. Alternately, the analog-to-digital converter is disposed between the radio frequency receiving coil and the receiver for digital receivers. Ultimately, the radio frequency signals received are demodulated and reconstructed into an image representation by a reconstruction processor 50 which applies a Fourier transform or other appropriate reconstruction algorithm. The image may represent a planar slice through the patient, an array of parallel planar slices, a three-dimensional volume, or the like. The image is then stored in an image memory 52 where it may be accessed by a video processor 54 that converts slices, projections, or other portions of the image representation into appropriate format for a display, such as a video monitor 56 which provides a man-readable display of the resultant image.

An endocavity RF coil assembly is used to pick up radio frequency signals generated by relaxing magnetic dipoles. The endocavity RF coil assembly includes a reusable probe 30 which is inserted into a cavity of a subject being examined so as to be contiguous to a region of interest, such as the prostate, the cervix, or the like. The coil's proximity to the region of interest provides for a relatively high signal-to-noise ratio.

Figure 2A:
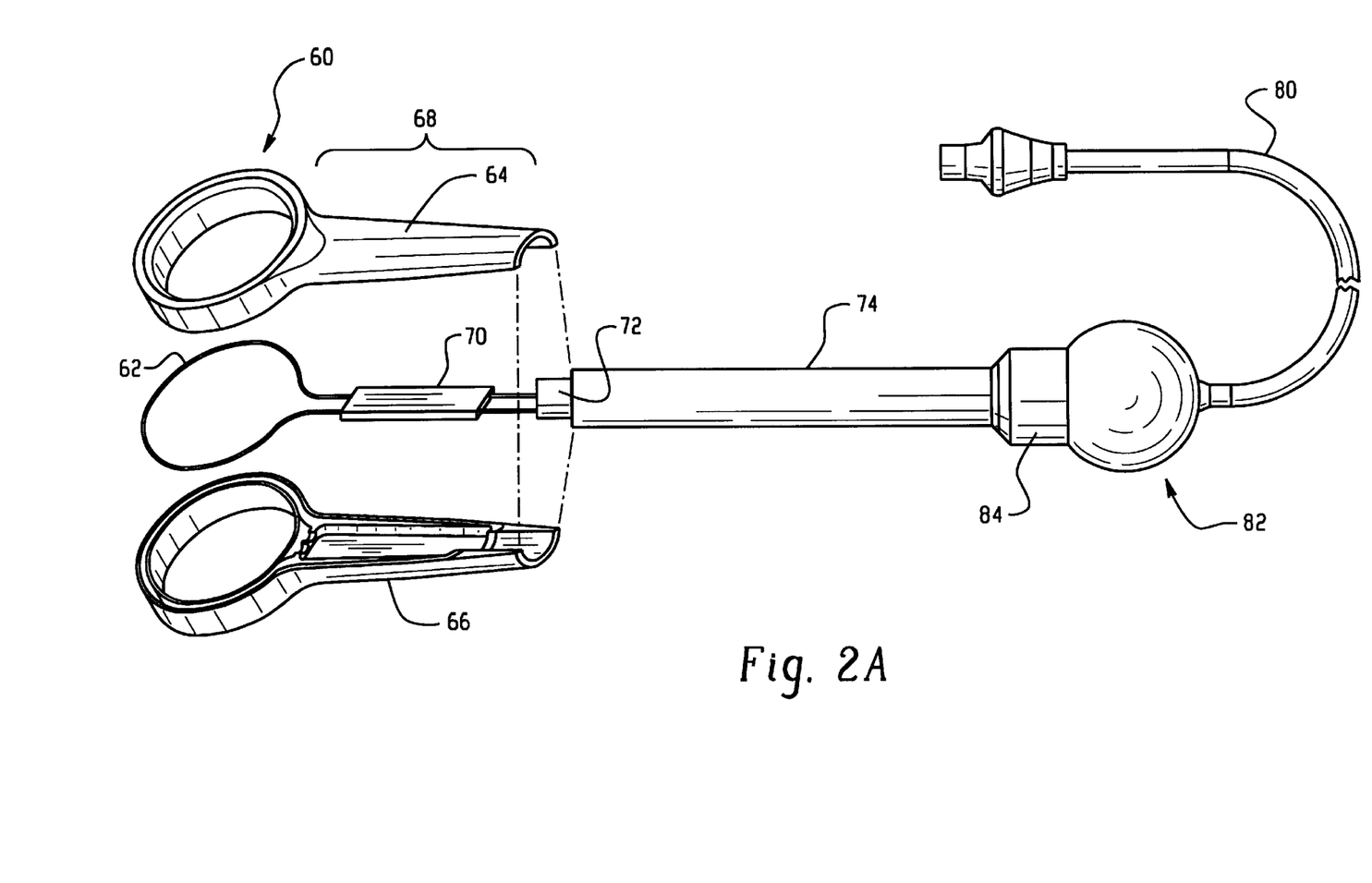
FIG. 2A is an expanded view of a cervix probe in accordance with the endocavity RF coil assembly of the present invention.
Figure 2B:
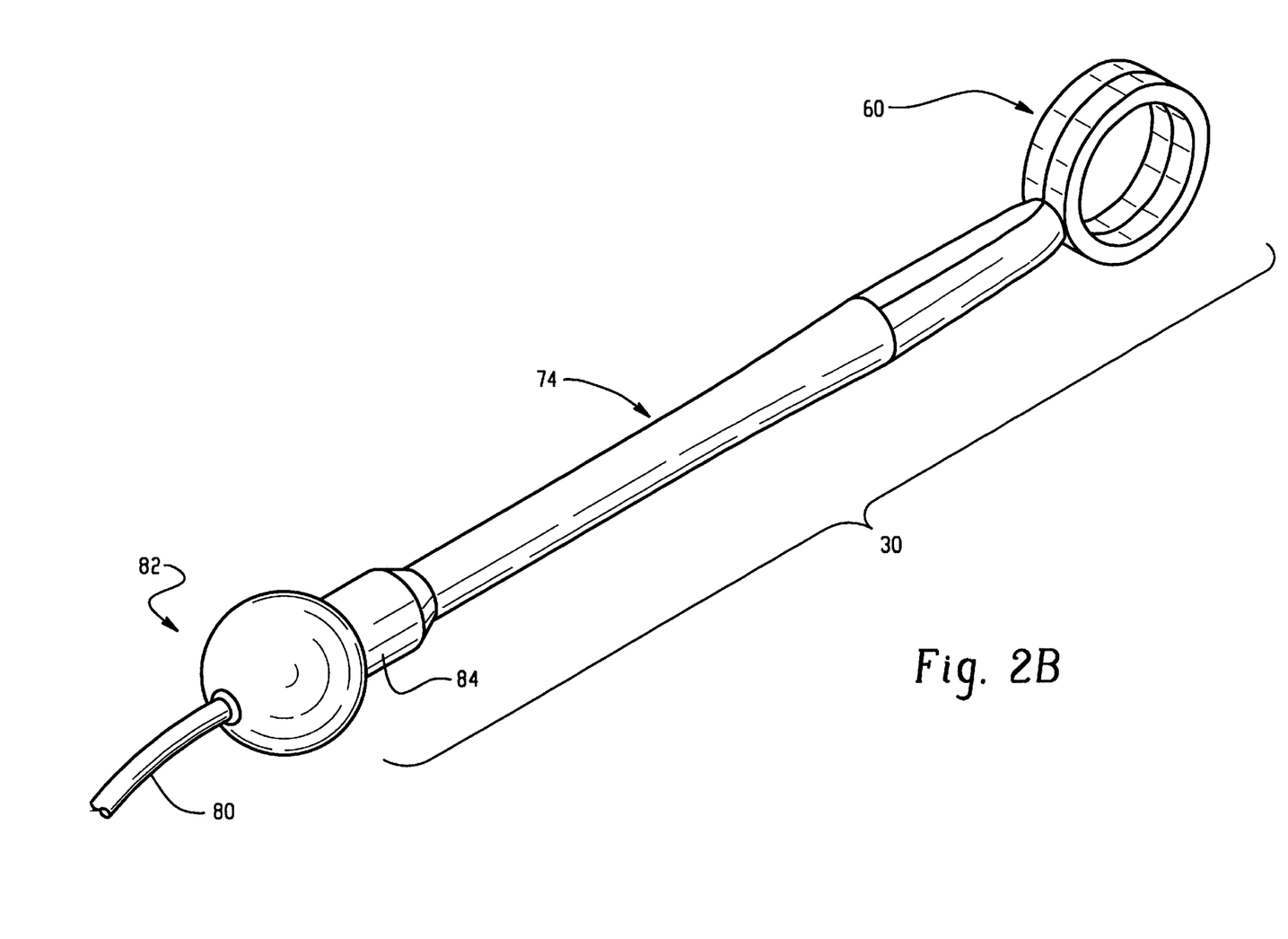
FIG. 2B is an assembled view of the probe of FIG. 2A.

In one preferred embodiment, with reference to FIGS. 2A and 2B, the endocavity RF coil assembly includes a cervix probe 30. The cervix probe 30 includes a hollow annular portion 60 in which an active RF coil element 62 is rigidly secured. The coil loop is rigidly secured between an internal ring section halves 64, 66. The section halves include a shaft portion 68 which houses a printed circuit board 70 containing tuning and matching circuitry. Both the internal ring section halves are preferably constructed of medical grade ABS plastic. The ABS plastic is appropriately flame retardant and is specifically intended for limited exposure to mucus membrane or blood barrier contact. The shaft portion 68 is telescopically connected to a seating surface 72 of a shaft assembly 74. The seating surface 72 is reduced from the surface of the shaft 74 by the thickness of the shaft portion 68 to form a smooth surface.

An RF cable 80 connects the output of the tuning and matching circuit to the MRI system preamplifier. Preferably, the cable 80 has been constructed from a non-magnetic version of a standard RG174 cable. Over the outer cable insulation, a non-toxic PVC outer jacket has been molded. The PVC jacket provides an appropriate non-toxic contact with a patient and also provides an electrical field insulating distance between the patient and the outer electrical shield of the cable thereby preventing the risk of RF burn.

An over-molded form 82 seals an open proximate end 83 of the shaft 74. Preferably, the over-molded form 82 is constructed of PVC plastic. The RF cable 80 extends from the tuning and matching circuit through the over-molded form 82. A portion of the over-molded form 82 is embedded in circumferential grooves and flats formed on the outer surface of an enlarged portion 84 of the shaft 74 to provide, a tight mechanical seal which is appropriately resistant to the ingress of fluid. The interface between the over-molded form 82 and RF cable 80 is appropriately resistant to the ingress of fluid due to a chemical PVC-to-PVC seal provided therebetween.

Figure 3A:
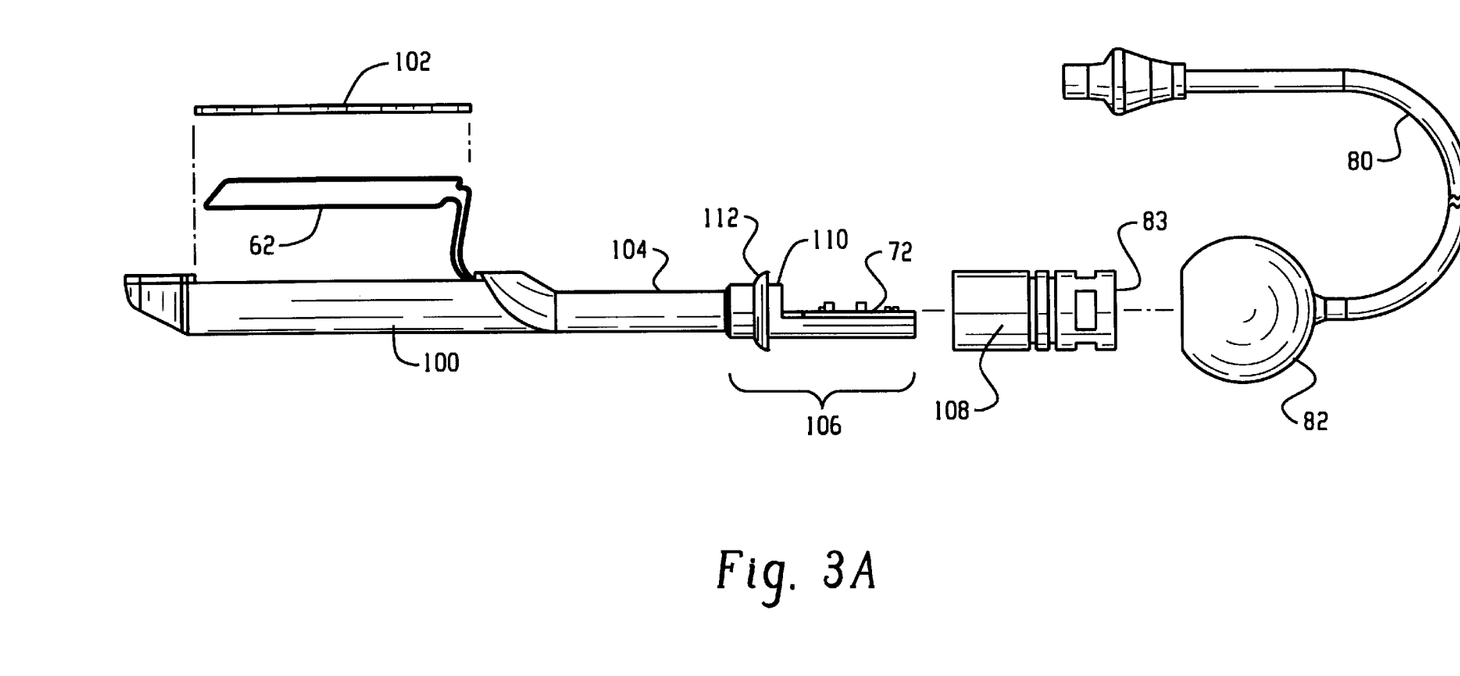
FIG. 3A is an expanded view of a prostate probe in accordance with the endocavity RF coil assembly of the present invention.
Figure 3B:
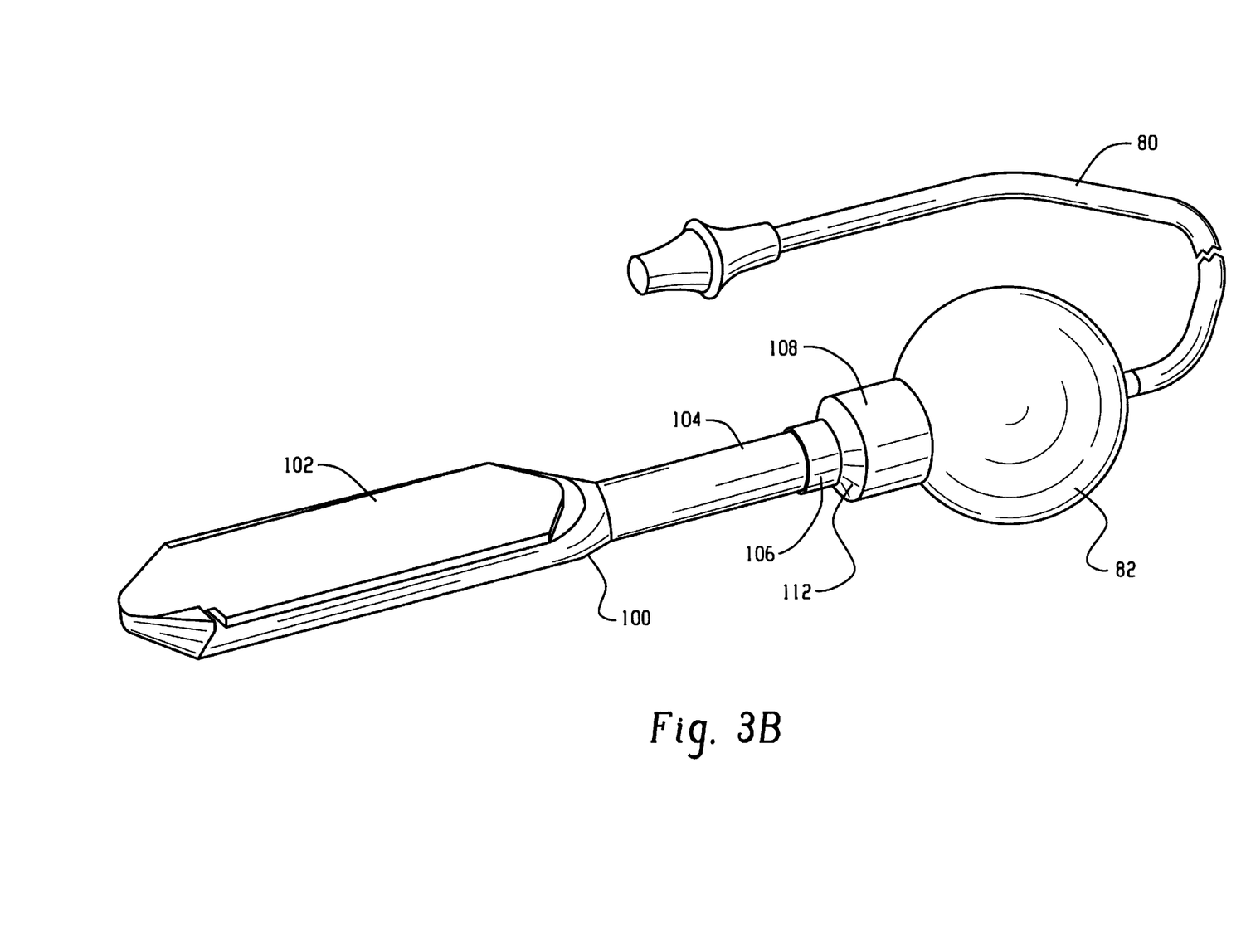
FIG. 3B is an assembled view of the probe of FIG. 3A.

With reference to FIGS. 3A and 3B, in another preferred embodiment, the endocavity RF coil assembly includes a probe 30 for examination of the prostate. The prostate probe includes a main body 100, preferably constructed of medical grade ABS plastic, which has a groove for locating and mounting the active RF coil element 62. A cover 102, also preferably made out of medical-grade ABS plastic, seals the main body 100. The main body 100 has an integral shaft portion 104 with an enlarged region 106 for receiving a circuit board 70. A shaft cover 108 slides over a seating surface 110 and abuts a flange 112. The printed circuit board 70 holds the tuning and matching circuitry. The shaft cover 108 includes grooves and flats for anchoring the over-molded form 82, and the RF cable 80 in the same manner as the previously discussed preferred embodiment.

While the illustrated over-molded form 82 has been depicted as being spherical in shape, the over-molded form 82 may take on other appropriate shapes. For example, in one preferred embodiment, the over-molded form 82 takes the shape of a polyhedron. Each side of the polyhedron is marked with appropriate indicia. In this manner, the over-molded form 82 can be exploited for indexing the relative orientation of the probe 30 and the active RF coil element 62 rigidly secured therein with respect to the patient. In another alternate embodiment, the probe 30 may include materials in its construction which emit a limited magnetic resonance signal. Again, this allows the relative position and orientation of the probe 30 within the subject to be determined relative to the anatomy being imaged.

One advantageous aspect of the present invention is the fact that the probe 30 is sealed to prevent the ingress of fluids. While described with reference to grooves and flats in which the over-molded form 82 is embedded to make a mechanical seal, it is appreciated that other means such as ultrasonically welding or use of medical-grade adhesive in construction may be used to create the appropriate seals.

Figure 4A:
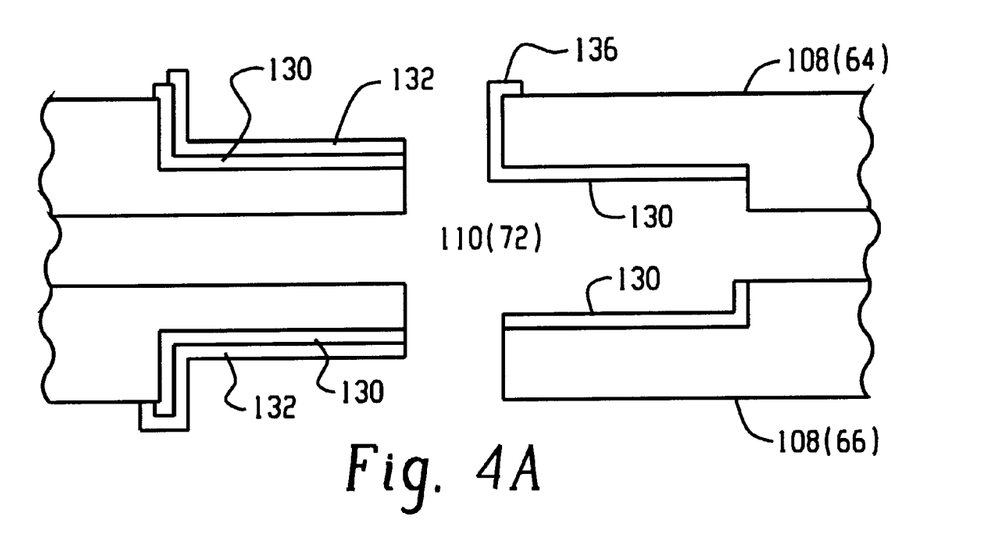
FIG. 4A is a cross sectional illustration of FIG. 3A or 2B ready for bonding; and, FIG. 4B is a cross sectional illustration of the two elements of FIG. 4A in a bonded configuration.
Figure 4B:
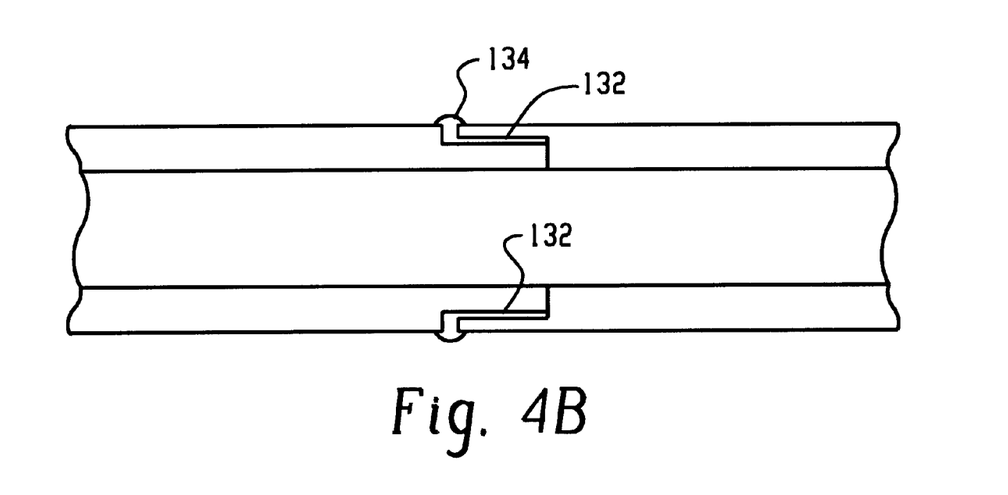

With reference to FIGS. 4A and 4B, in order to prevent harmful contaminants from being lodged into indentations and crevices that result at the seams where more than one segment of ABS plastic come together, interfaces between elements are filled such that no crevices are defined. In order to affect a reliable adhesion, the seating surfaces and the surfaces that mate with them are pre-treated to modify their surface chemistry. Medical grade ABS is substantially chemically inert. Its surface chemistry lacks chain ends with which other substances can react. The surface treatment breaks the polymer chains to create reactive ends. Various surface treatments are contemplated including plasma discharge treatment, corona discharge treatment, electron beam or radiation bombardment, highly reactive chemistries that react and attach midway along polymer chains, and the like.

In a preferred embodiment, the pre-treatment is a hydrophilic layer 130. The hydrophilic layer 130 bonds to the plastic. An epoxy layer 132 bonds to the hydrophilic layers 130. Sufficient epoxy is applied to coat all surfaces and fill all crevices. To assure that the crevices are filled, a small bead of epoxy is optionally formed along the seam. The bead is optionally widened and flattened by surface treating a short line of adjoining exposed surface 136.

In another preferred embodiment, the crevices are filled by ultrasonic or other plastic welding techniques.

Most reaction injection cured seams show up in MRI images. Most resin cured seams are not currently biocompatability approved.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A reusable endocavity RF coil probe for an MRI apparatus, which probe is chemically high level disinfected or sterilized between patients, the probe comprising:

a hollow outer cover formed of multiple pieces, the pieces forming seams where they join, the cover having a closed distal end and an open proximate end, the distal end formed to fit into a cavity of the patient being examined;

an active RF coil element rigidly formed internally within the distal end of the outer cover;

a tuning and matching circuit disposed within the outer cover on the proximate end side of the active RF coil element, the tuning and matching circuit being arranged on a printed circuit board and attached to the active RF coil element;

an over-molded form connected to the proximate end of the outer cover, the over-molded form being arranged such that the over-molded form seals the proximate end of the outer cover closed;

surfaces adjacent and along the seams being treated by one of coated with a hydrophilic coating and chemically modified with one of radiation and plasma treatment; and, a medical grade epoxy coating, whose bonding to the outer cover pieces is facilitated by the surface treatment adjacent the seams, sealing and filling the seams to eliminate crevices that could shelter microbes during high level disinfection and sterilization.

2. An endocavity RF probe comprising:

an RF coil;

a circuit board carrying electronics, the circuit board electronics being connected with the RF coil;

a sealed housing constructed of a chemically inert plastic which internally encases the RF coil and the circuit board therein, the housing being shaped for insertion into the endocavity, the housing being configured of a plurality of pieces, the pieces having mating surfaces that are at least partially surface treated to improve adhesion by a bonding agent, the mating surfaces abutting with each other at crevice free seams.

3. The endocavity RF probe according to claim 2, wherein surface treatment breaks polymer chains of the plastic creating chain ends.

4. The endocavity RF probe according to claim 3, further including:

a bonding agent which attaches to the chain ends to bond the pieces together.

5. The endocavity RF probe according to claim 3, wherein the surface treatment includes one of: irradiation, plasma discharge, corona discharge, and chemical modification.

6. The endocavity RF probe according to claim 2, further including:

a bonding agent coating the treated surfaces and completely filling the seams.

7. The endocavity RF probe according to claim 6, wherein:

The bonding agent forms a bead extending from the seams.

8. An endocavity RF probe comprising:

an RF coil;

a circuit board carrying electronics, the circuit board electronics being connected with the RF coil;

a sealed housing constructed of ABS plastic which internally encases the RF coil and the circuit board therein, the housing being shaped for insertion into the endocavity, the housing being configured of a plurality of pieces, the pieces having mating surfaces that are surface treated to break polymer chains of the ABS plastic to create free ends of the polymer chains, the mating surfaces abutting with each other at crevice-free seams; and, an epoxy bonded to the polymer chain free ends of the treated surfaces and completely filling the seams.

9. A method of RF coil construction to facilitate sterilization of an RF coil, the method comprising:

placing RF coil components in a housing made of multiple pieces of medical grade ABS plastic, seams being defined where the housing pieces fit together;

treating surfaces of the housing pieces adjacent the seams;

applying a bonding agent to the treated surfaces;

bonding the housing pieces together with the seams filled to inhibit microbes from being sheltered in the seams.

10. The method as set forth in claim 9, wherein the step of treating surfaces of the housing includes:

applying a hydrophilic coating that chemically bonds to the housing.

11. The method as set forth in claim 9, wherein the step of treating includes:

modifying the surface chemistry of the housing by one of radiation, corona, and plasma treatment.

12. A method of RF coil construction to facilitate sterilization of an RF coil, the method comprising:

placing RF coil components in a housing made of multiple pieces of medical grade ABS plastic, seams being defined where the housing pieces fit together;

treating surfaces of the housing adjacent the seams to create free ends in the polymer chains of the ABS plastic;

applying a medical grade epoxy to the treated surfaces;

bonding the housing pieces together with the seams filled to sufficiently inhibit microbes from being sheltered in the seams.

* * * * *